United States Patent
Kvamme et al.

(10) Patent No.: US 9,046,500 B2
(45) Date of Patent: Jun. 2, 2015

(54) ADAPTABLE ILLUMINATING APPARATUS, SYSTEM, AND METHOD FOR EXTREME ULTRA-VIOLET LIGHT

(71) Applicant: KLA-Tencor Corporation, Milpitas, CA (US)

(72) Inventors: Damon Kvamme, Los Gatos, CA (US); Yanming Zhao, Milpitas, CA (US)

(73) Assignee: KLA-Tencor Corporation, Milpitas, CA (US)

(*) Notice: Subject to any disclaimer, the term of this patent is extended or adjusted under 35 U.S.C. 154(b) by 0 days.

(21) Appl. No.: 14/109,457

(22) Filed: Dec. 17, 2013

(65) Prior Publication Data

US 2014/0175308 A1 Jun. 26, 2014

Related U.S. Application Data

(60) Provisional application No. 61/740,072, filed on Dec. 20, 2012.

(51) Int. Cl.

| | |
|---|---|
| *G02B 5/02* | (2006.01) |
| *G02B 5/10* | (2006.01) |
| *F21V 7/09* | (2006.01) |
| *G01N 21/95* | (2006.01) |
| *G02B 27/09* | (2006.01) |
| *G02B 17/06* | (2006.01) |
| *G02B 5/08* | (2006.01) |

(52) U.S. Cl.
CPC ........ *G01N 21/9501* (2013.01); *G02B 27/0988* (2013.01); *G02B 17/0621* (2013.01); *G02B 5/0891* (2013.01); *G02B 27/0994* (2013.01)

(58) Field of Classification Search
CPC ...... G02B 5/10; G02B 6/4298; G02B 11/005; G02B 17/00; G02B 17/0621; G02B 19/0023; G02B 19/0028; G02B 19/0047; G02B 27/283; G02B 27/1046; G02B 27/0905; G02B 27/0983; G02B 27/0994; G01M 11/005; G01N 21/956; G01N 21/8806

See application file for complete search history.

(56) References Cited

U.S. PATENT DOCUMENTS

| 5,625,738 | A |  | 4/1997 | Magarill | |
|---|---|---|---|---|---|
| 5,822,066 | A | * | 10/1998 | Jeong et al. | 356/521 |
| 6,142,641 | A | * | 11/2000 | Cohen et al. | 359/859 |
| 6,332,688 | B1 | * | 12/2001 | Magarill | 359/858 |
| 6,705,737 | B1 | * | 3/2004 | Manhart | 359/869 |
| 6,840,640 | B2 | * | 1/2005 | Antoni et al. | 359/858 |

(Continued)

FOREIGN PATENT DOCUMENTS

| EP | 1306697 A1 | 5/2003 |
|---|---|---|
| JP | 2006-216784 | 8/2006 |
| WO | 2005067308 A1 | 7/2005 |

*Primary Examiner* — David A Vanore
(74) *Attorney, Agent, or Firm* — Simpson & Simpson, PLLC (57) ABSTRACT

An apparatus for focusing light in a semi-conductor inspection system, including: a first mirror arranged to reflect extreme ultra-violet (EUV) generated by a plasma source; and a second mirror arranged to focus the EUV light, reflected from the first mirror, onto a first intermediate focus plane. A homogenizing tunnel, including: a first aperture having a first shape and a first size and arranged to receive extreme ultra-violet (EUV) light; a second aperture having a second shape and a second size; and a passageway connecting the first and second apertures and arranged to homogenize the EUV light received by the first aperture. The first shape is different from the second shape or the first size is different from the second size.

30 Claims, 9 Drawing Sheets

(56) References Cited

U.S. PATENT DOCUMENTS

| | | | |
|---|---|---|---|
| 6,899,440 B2* | 5/2005 | Bierhuizen | 362/19 |
| 7,261,423 B2* | 8/2007 | Magarill et al. | 353/94 |
| 7,583,433 B2* | 9/2009 | Antoni et al. | 359/351 |
| 7,648,248 B2* | 1/2010 | Yafuso | 359/851 |
| 2003/0076607 A1* | 4/2003 | Antoni et al. | 359/858 |
| 2004/0125369 A1 | 7/2004 | Wang | |
| 2004/0223225 A1* | 11/2004 | Mikhailov | 359/619 |
| 2005/0083503 A1* | 4/2005 | Antoni et al. | 355/67 |
| 2005/0270501 A1* | 12/2005 | Yoshida | 353/99 |
| 2006/0274277 A1 | 12/2006 | Magarill et al. | |
| 2008/0087847 A1 | 4/2008 | Bykanov et al. | |
| 2009/0073587 A1 | 3/2009 | Pfitzner | |
| 2010/0073790 A1* | 3/2010 | Yafuso | 359/853 |
| 2012/0138805 A1* | 6/2012 | Missalla et al. | 250/362 |
| 2013/0242295 A1* | 9/2013 | Wang et al. | 356/239.1 |

* cited by examiner

Figure 10:
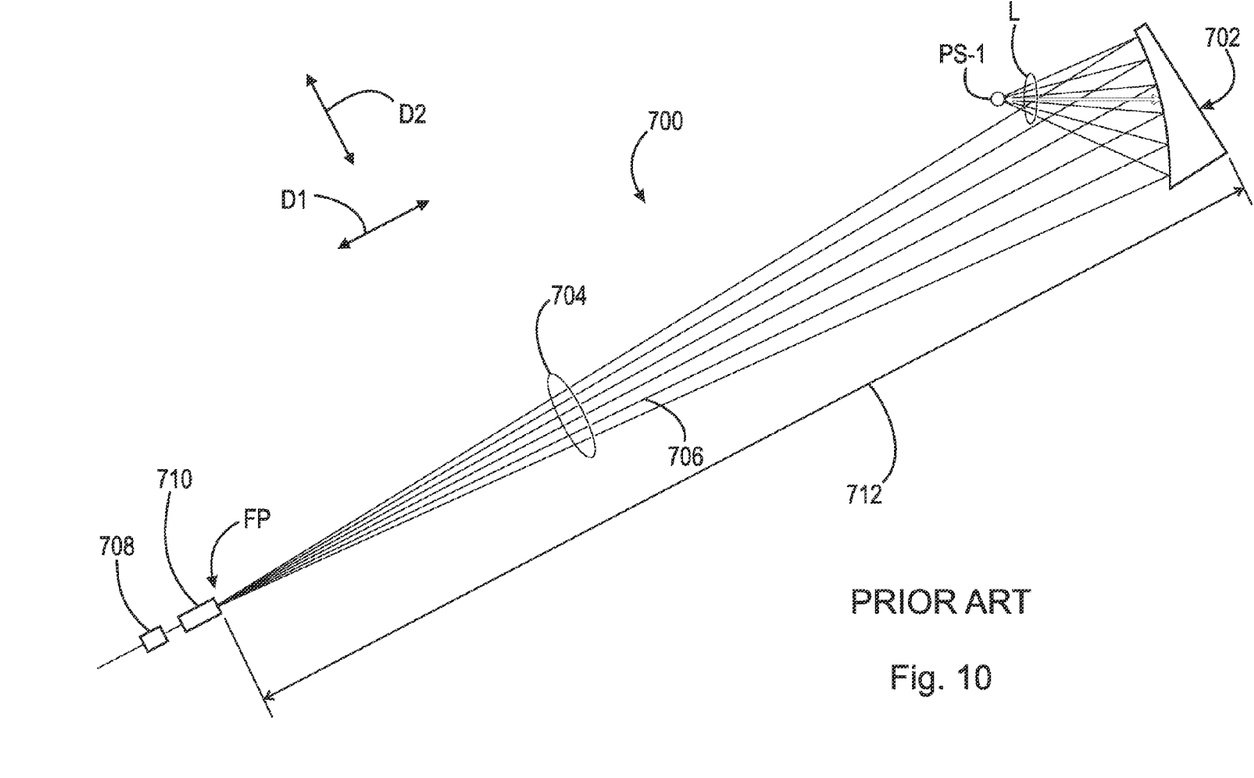

PRIOR ART
Fig. 10 ically sized space, for example in the D1 and D2 directions, for source PS, mirror 702, and plane FP. System 700 also includes non-tapered rectangular homogenizing tunnel 710 positioned at plane FP and used to homogenize EUV light from plane FP for use by optics 708. In general, it is desirable to maintain a uniform image size at plane FP, since changes in the image size result in undesired changes to the spatial and angular distribution at the illumination field.

ADAPTABLE ILLUMINATING APPARATUS, SYSTEM, AND METHOD FOR EXTREME ULTRA-VIOLET LIGHT

CROSS-REFERENCE TO RELATED APPLICATIONS

This application claims the benefit under 35 U.S.C. §119(e) of U.S. Provisional Patent Application No. 61/740,072, filed Dec. 20, 2012, which application is incorporated herein by reference in its entirety.

TECHNICAL FIELD

The present disclosure relates to adaptable extreme ultra-violet (EUV) illuminating apparatuses, systems and methods for semi-conductor inspection systems. In particular, the present disclosure relates to an apparatus, system, and method for providing a same plasma image at a fixed focus plane using different plasma sources having different properties by changing collector components within a same fixed space. In particular, the present disclosure relates to an apparatus, system, and method for providing a same plasma image for an illumination field for a semi-conductor inspection system, using different plasma sources having different properties, via variously tapered homogenizing tunnels, while maintaining a fixed position for a focus plane and a same fixed space for collection optics.

BACKGROUND

FIG. 10 is a schematic representation of prior art illumination system 700 for extreme ultra-violet (EUV). System 700 includes plasma source PS and mirror 702. Plasma from source PS generates EUV light L, for example plasma is generated by focusing a high power laser (not shown) onto a tin or xenon target. Mirror 702 is arranged to reflect and focus light L onto bundle 704 of light rays 706 focused on focus plane FP. That is, mirror 702 is arranged to reimage the plasma to plane FP. For example, system 700 can be part of a semi-conductor inspection system and optics 708 are located in FP and arranged to convert collected photons at plane FP into desired spatial and angular distribution at an illumination field (not shown).

Mirror 702 is configured for a specific size of the plasma and a specific angular distribution of the intensity of the plasma, which in turn results in a specifically sized space, for example in the D1 and D2 directions, for source PS, mirror 702, and plane FP. System 700 also includes non-tapered rectangular homogenizing tunnel 710 positioned at plane FP and used to homogenize EUV light from plane FP for use by optics 708. In general, it is desirable to maintain a uniform image size at plane FP, since changes in the image size result in undesired changes to the spatial and angular distribution at the illumination field.

Advances in semi-conductor inspection technology are resulting in changes to the size of the plasma or the angular distribution of the intensity of the plasma. In order to maintain the desired spatial and angular distribution at the illumination field when the plasma source is modified, the size of the image in plane FP must be preserved. To preserve the size of the image in plane FP, other portions of system 700 must be modified. In particular, the relative positions of source PS, mirror 702, and plane FP must be modified. In general, distance 712 must be expanded to accommodate the changes in position. However, expanding distance 712 results in increases complexity and cost, since space in semi-conductor inspection systems is tightly rationed. Thus, in the face of the changes to the plasma noted above, the previous optical and physical properties of system 700 cannot be simultaneously retained.

SUMMARY

According to aspects illustrated herein, there is provided an apparatus for focusing light in a semi-conductor inspection system, including: a first mirror arranged to reflect extreme ultra-violet (EUV) generated by a plasma source; and a second mirror arranged to focus the EUV light, reflected from the first mirror, onto a first intermediate focus plane.

According to aspects illustrated herein, there is provided a semi-conductor inspection system, including: a plasma source arranged to generate extreme ultra-violet (EUV) light; a focusing assembly including a first mirror arranged to reflect the EUV light from the plasma source and a second mirror arranged to focus the EUV, light reflected from the first mirror, onto a first intermediate focus plane; and an optical component in the first intermediate focus plane, arranged to receive the EUV light reflected from the second mirror.

According to aspects illustrated herein, there is provided a homogenizing tunnel, including: a first aperture having a first shape and a first size and arranged to receive extreme ultra-violet (EUV) light; a second aperture having a second shape and a second size; and a passageway connecting the first and second apertures and arranged to homogenize the EUV light received by the first aperture. The first shape is different from the second shape or the first size is different from the second size.

According to aspects illustrated herein, there is provided a semi-conductor inspection system, including: a plasma source arranged to generate extreme ultra-violet (EUV) light; an illuminating apparatus including at least one mirror arranged to reflect the EUV light from the plasma source and focus the EUV light onto a first intermediate focus plane; and a homogenizing tunnel including a first aperture positioned at the first intermediate focus plane and having a first shape and a first size; a second aperture having a second shape and a second size; and a passageway connecting the first and second apertures. The EUV light focused by the second mirror at the first intermediate focus plane is arrange to enter the homogenizing tunnel at the first aperture and exit the homogenizing tunnel at the second aperture. The first shape is different from the second shape or the first size is different from the second size.

According to aspects illustrated herein, there is provided a method for focusing light in a semi-conductor inspection system, including: reflecting, using a first mirror, extreme ultra-violet (EUV) light generated by a plasma source; and focusing, using a second mirror, the EUV light reflected from the first mirror, onto a first intermediate focus plane for use in a semi-conductor inspection system.

According to aspects illustrated herein, there is provided a method for homogenizing light in a semi-conductor inspection system, including: focusing, onto a first intermediate focus plane and using at least one mirror, extreme ultra-violet (EUV) light generated by a plasma source; transmitting the EUV light focused on the first intermediate focus plane into a first aperture of a homogenizing tunnel; transmitting the EUV light focused onto the first intermediate focus plane along a tapered passageway for the homogenizing tunnel; reflecting the EUV light focused onto the first intermediate focus plane from a plurality of surfaces of the passageway; and transmitting the EUV light focused onto the first intermediate focus plane and the EUV light reflected from the plurality of surfaces out of the homogenizing tunnel through a second aperture of the tunnel for use in a semi-conductor inspection system.

According to aspects illustrated herein, there is provided a method for focusing light in a semi-conductor inspection system, including: generating first extreme ultra-violet (EUV) light using a first plasma source having a first intensity and a first angular distribution of intensity; focusing, using first and second mirrors, the first EUV light onto an intermediate focus plane for use in semi-conductor inspection; generating second extreme ultra-violet (EUV) light using a second plasma source having a second intensity or a second angular distribution of intensity; and, focusing, using third and fourth mirrors, different from the first and second mirrors respectively, the second EUV light onto the intermediate focus plane. The first plasma source and the first and second mirrors occupy a first minimum space within the semi-conductor inspection system. The second plasma source and the third and fourth mirrors occupy a second minimum space within the semi-conductor inspection system. The first minimum space is substantially equal to the second minimum space.

According to aspects illustrated herein, there is provided a method for focusing light in a semi-conductor inspection system, including: generating first extreme ultra-violet (EUV) light using a first plasma source having a first intensity and a first angular distribution of intensity; focusing, using at least one first mirror, a first image, with a first size, of the first EUV light onto an intermediate focus plane; transmitting the first EUV light, as a first image, through a first tapering passageway for a first homogenizing tunnel with a first entrance aperture congruent with the intermediate focus plane; transmitting, from an exit aperture for the first tunnel, the first EUV light as the first image with the first size for use in the semi-conductor inspection system; generating second extreme ultra-violet (EUV) light using a second plasma source having a second intensity or a second angular distribution of intensity; focusing, using the at least one second mirror, a second image, with a second size different from the first size, of the second EUV light onto the intermediate focus plane; transmitting the second EUV light, as the second image, through a second tapering passageway for a second homogenizing tunnel with a second entrance aperture congruent with the intermediate focus plane; and transmitting, from an exit aperture for the first tunnel, the second EUV light as the second image with the first size for use in the semi-conductor inspection system. A position of the intermediate focus plane is fixed with respect to the semi-conductor inspection system. The at least one first mirror and the at least one second mirror are in the same respective positions, or a first minimum space occupied by the at least one first mirror is substantially equal to a second minimum space occupied by the at least one second mirror.

These and other objects and advantages of the present disclosure will be readily appreciable from the following description of the invention and from the accompanying drawings and claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements of the disclosure. It is to be understood that the disclosure as claimed is not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the present disclosure.

Unless defined otherwise, all technical and scientific terms used herein have the same meaning as commonly understood to one of ordinary skill in the art to which this disclosure belongs. It should be understood that any methods, devices or materials similar or equivalent to those described herein can be used in the practice or testing of the disclosure.

Figure 1:
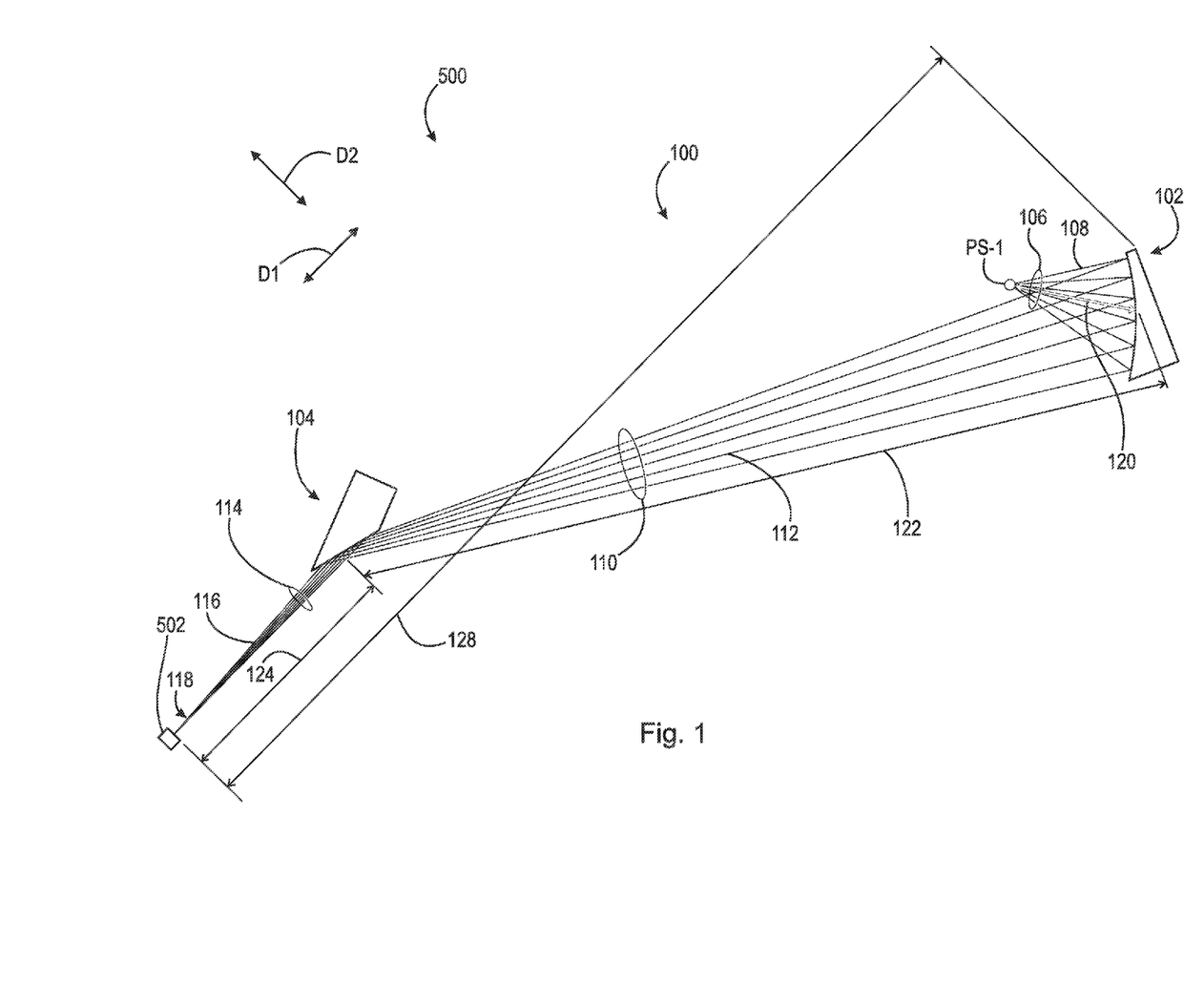
FIG. 1 is a schematic representation of an illuminating apparatus for extreme ultra-violet light with a positive power mirror and a negative power mirror.

FIG. 1 is a schematic representation of illuminating apparatus 100 for extreme ultra-violet light with a positive power mirror and a negative power mirror. Apparatus 100 includes positive mirror 102 and negative mirror 104. Mirror 102 is arranged to reflect and focus bundle 106 of extreme ultra-violet (EUV) light rays 108 generated by plasma source PS-1 to form bundle 110 of EUV light rays 112. Mirror 104 is arranged to reflect and focus bundle 110 to form bundle 114 of EUV light rays 116 focused onto intermediate focus plane 118. Bundle 106 travels straight distance 120, bundle 110 travels straight distance 122, and bundle 114 travels straight distance 124. In an example embodiment, mirror 102 is elliptical concave. In an example embodiment, mirror 104 is hyperbolic convex.

Figure 2:
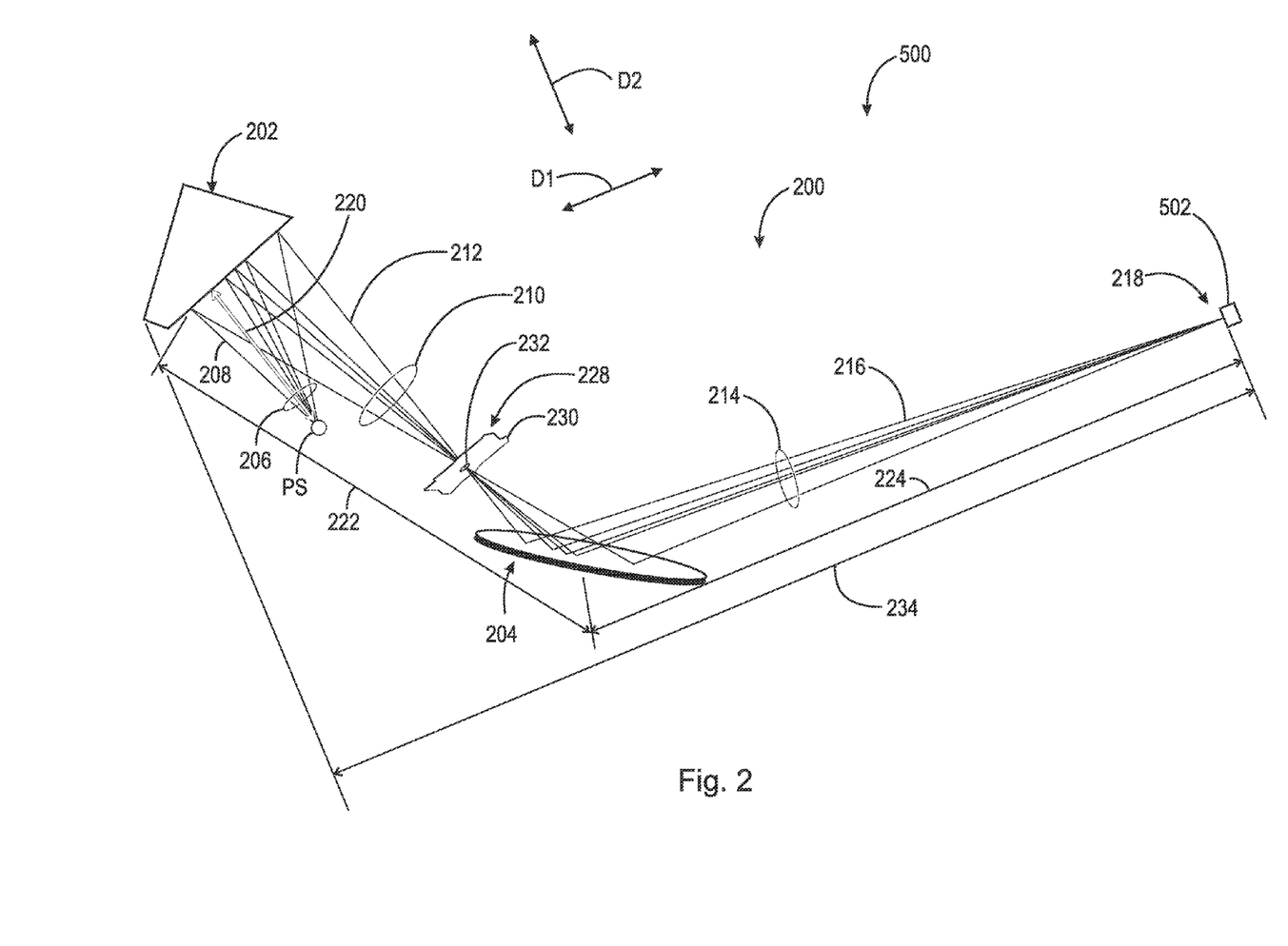
FIG. 2 is a schematic representation of an illuminating apparatus for extreme ultra-violet light with two positive power mirrors and an intermediate image.

FIG. 2 is a schematic representation of illuminating apparatus 200 for extreme ultra-violet light with two positive power mirrors and an intermediate image. Apparatus 200 includes positive mirrors 202 and 204. Mirror 202 is arranged to reflect and focus bundle 206 of extreme ultra-violet (EUV) light rays 208 generated by plasma source PS-2 to form bundle 210 of EUV light rays 212. Mirror 204 is arranged to reflect and focus bundle 210 to form bundle 214 of EUV light rays 216 focused onto intermediate focus plane 218. Bundle 206 travels straight distance 220, bundle 210 travels straight distance 222, and bundle 214 travels straight distance 224. Mirror 202 also is arranged to focus bundle 210 onto intermediate focus plane 228 located between mirrors 202 and 204. In an example embodiment, apparatus 200 includes plate 230 with aperture 232. Plate 230 is positioned such that plane 228 coincides with aperture 232 and aperture 232 is substantially the same size as plane 228. Thus, bundle 210 passes through aperture 232. As further describe below, plate 230 blocks contamination associated with generation of EUV light by source PS.

Figure 3:
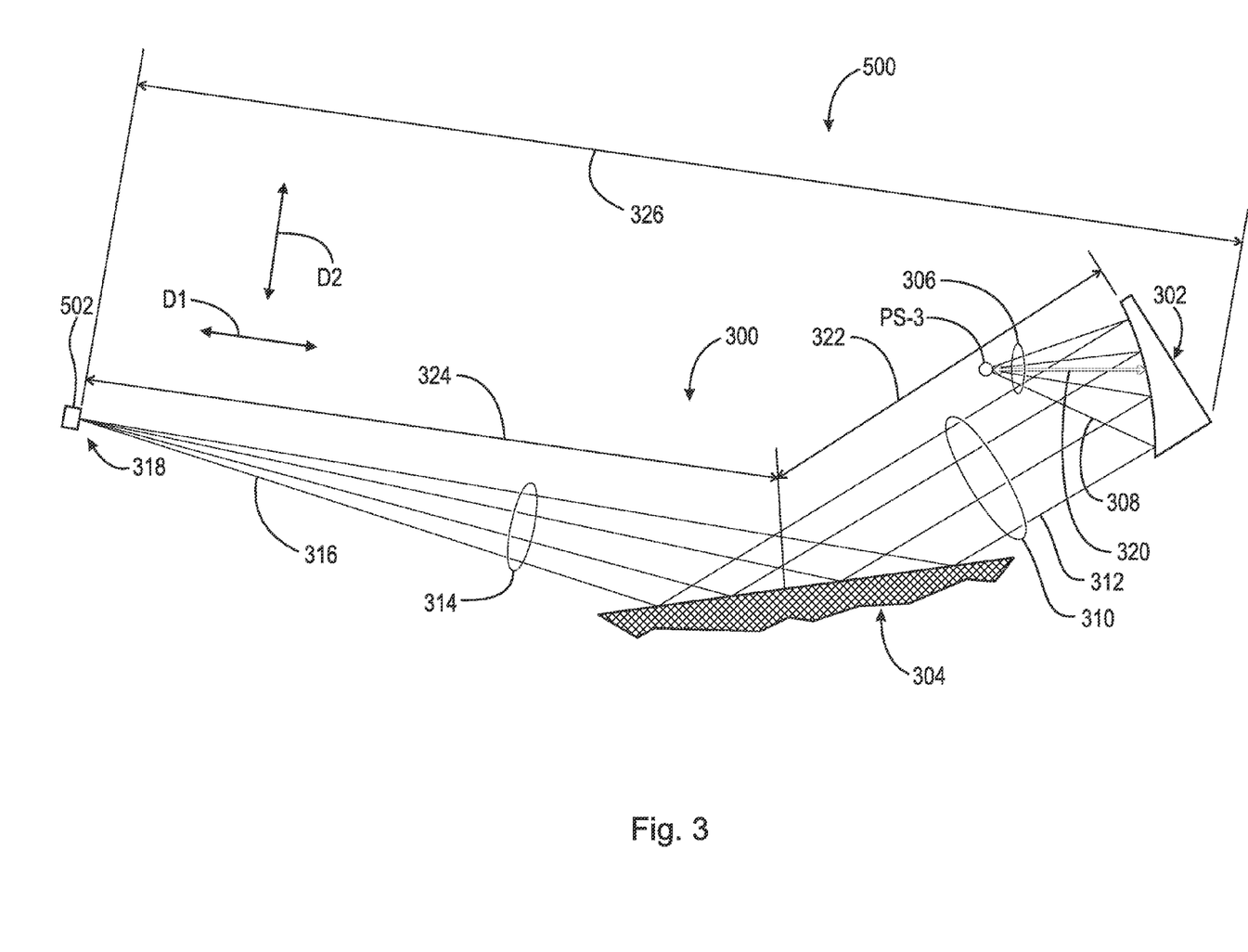
FIG. 3 is a schematic representation of an illuminating apparatus for extreme ultra-violet light with two positive power mirrors and no internal image.

FIG. 3 is a schematic representation of illuminating apparatus 300 for extreme ultra-violet light with two positive power mirrors and no internal image. Apparatus 300 includes positive mirrors 302 and 304. Mirror 302 is arranged to reflect and focus bundle 306 of extreme ultra-violet (EUV) light rays 308 generated by plasma source PS-3 to form bundle 310 of EUV light rays 312. Mirror 304 is arranged to reflect and focus bundle 310 to form bundle 314 of EUV light rays 316 focused onto intermediate focus plane 318. Bundle 306 travels straight distance 320, bundle 310 travels straight distance 322, and bundle 314 travels straight distance 324.

The following should be viewed in light of FIGS. 1 through 3. As noted above, changing the properties of the plasma source in a known EUV illumination system requires the undesirable modification of the physical or optical properties of the system. Advantageously, apparatuses 100, 200, and 300 are adaptable to changes in plasma source PS-1, PS-2, and PS-3, respectively, without modifications to physical or optical properties. For example, the footprint occupied by apparatuses 100, 200, and 300 remains unchanged while maintaining respective previous image sizes on the respective focal planes. For example, a plasma image on plane 118 remains the same when source PS-1 and mirrors 102 and 104 are modified. The preceding applied to apparatuses 200 and 300 as well.

Specifically, apparatuses 100, 200, and 300 each occupy minimum spaces in the D1 directions, bordered by focus planes 118, 218, and 318, respectively. The spaces are substantially equal to each other. Regardless of the respective mirror types and configurations employed in apparatuses 100, 200, and 300 in response to differences in plasma source PS-1, PS-2, and PS-3, apparatuses 100, 200, and 300 do not occupy more than the respective minimum distances 128, 234, and 326, respectively, for example, in directions D1. Thus, apparatuses 100, 200, and 300 do not require the costly space modifications, noted above, to systems in which apparatuses 100, 200, or 300 are interchangeably employed.

Using apparatus 100 as an example, a position of intermediate focus plane 118 is fixed with respect to a plane defined by directions D1 and D2 orthogonal to each other. One of plasma source PS-1 or mirror 102 is furthest from the plane 118 in the direction D1, for apparatus 100 it is mirror 102 (for apparatuses 200 and 300 it is mirrors 202 and 302, respectively). Specifically, mirror 102 is distance 128 from plane 118 in direction D1. Mirror 104 is between mirror 102 and focus plane 118 in direction D1 (the same holds true for mirrors 204 and 304 with respect to mirrors 202 and 302). For purposes of illustration, assume that PS-1 is replaced by PS-2, having different properties than PS-1, and subsequently, apparatus 100 is replaced by apparatus 200. One of plasma source PS-2 or mirror 202 is furthest from the plane 218 in the direction D1, for apparatus 200 it is mirror 202. Mirror 204 is between mirror 202 and focus plane 218 in direction D1. Specifically, mirror 202 is distance 234 from plane 218 in direction D1. Distance 128 is equal to distance 234. Note that for apparatus 300, plane 318 is separated from mirror 302 by distance 326 in the D1 direction.

Apparatuses 100, 200, and 300 also enable flexibility within the space allocated to the respective apparatuses for adapting to changes in the plasma source. For example, the use of two mirrors enables respective focal lengths of apparatuses 100, 200, and 300 to be markedly different from the respective overall lengths from the respective optics to the respective focus planes. With this flexibility, long focal length mirrors can be used in a space that would normally be too small, or alternatively a short focal length can be created where the working distance needs to exceed a minimal value.

Figure 4:
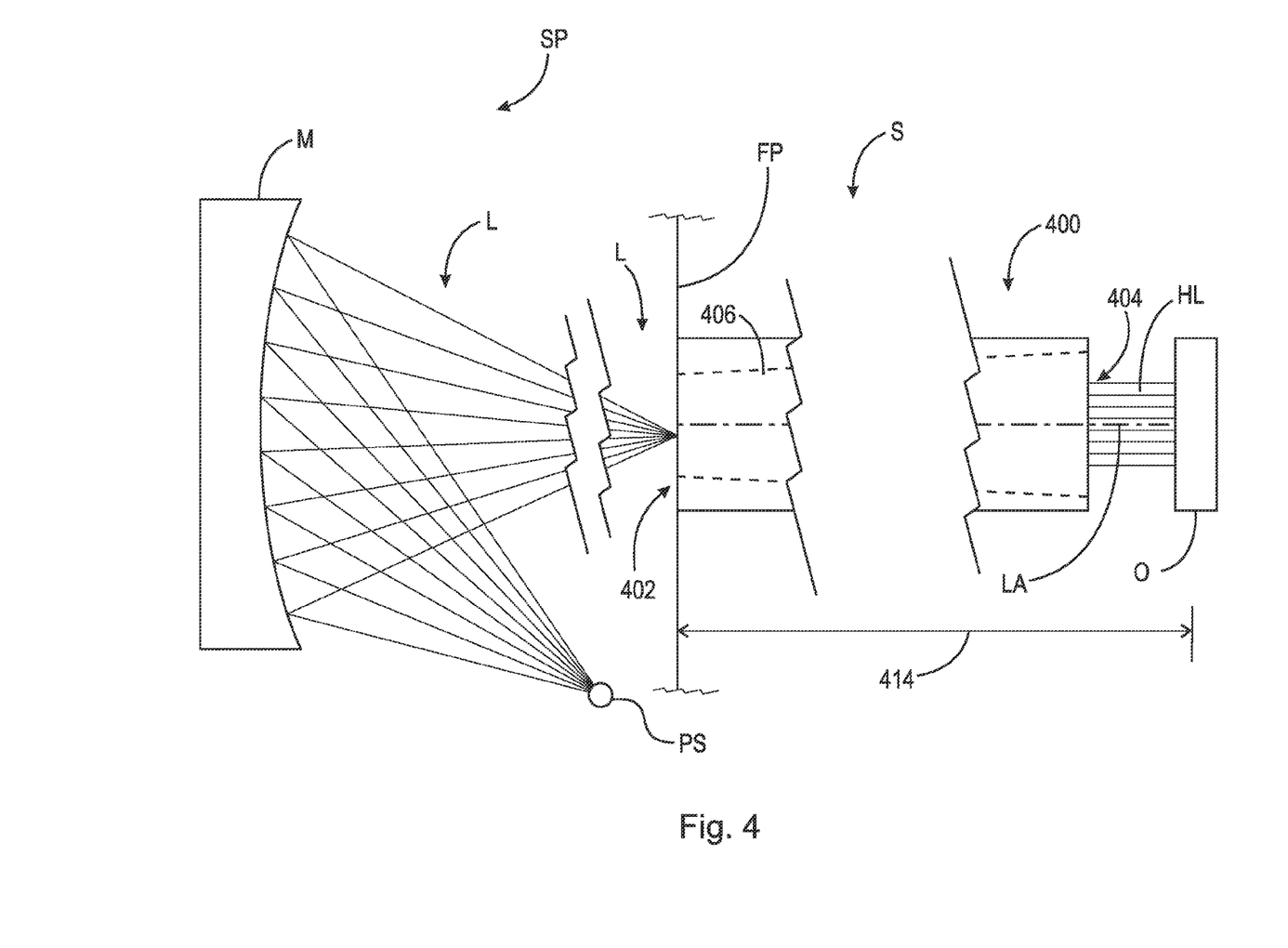
FIG. 4 is a schematic representation of a tapered homogenizing tunnel in a system for focusing extreme ultra-violet light.

FIG. 4 is a schematic representation of tapered homogenizing tunnel 400 in system S for focusing extreme ultra-violet light.

Figure 5:
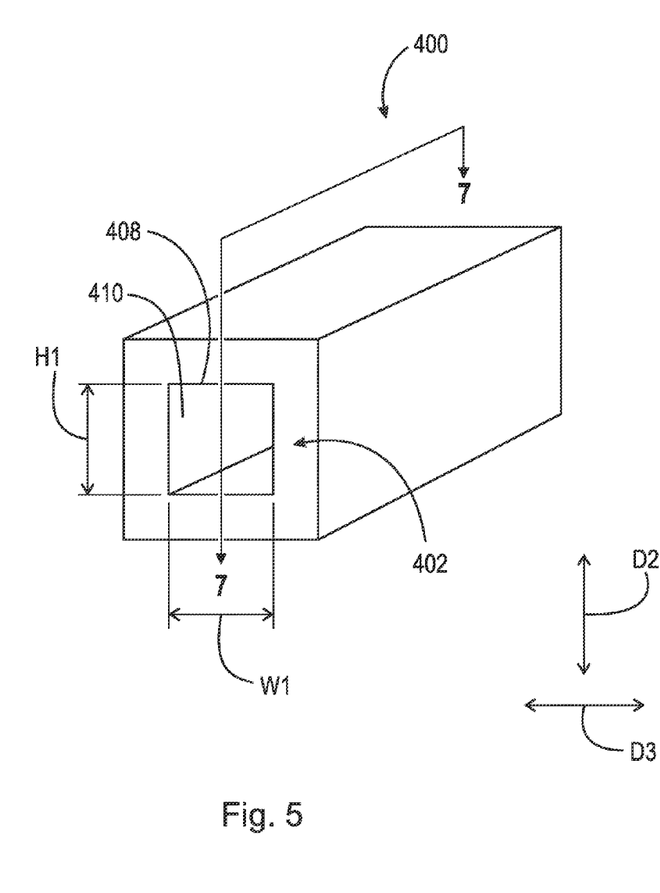
FIG. 5 is a schematic rear perspective view of the homogenizing tunnel in FIG. 4.

FIG. 5 is a schematic rear perspective view of homogenizing tunnel 400 in FIG. 4.

Figure 6:
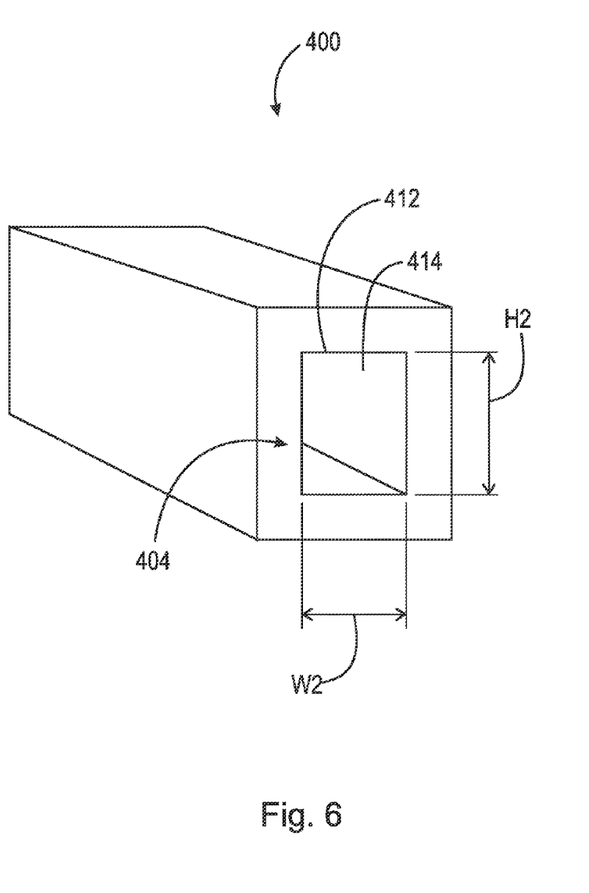
FIG. 6 is a schematic front perspective view of the homogenizing tunnel in FIG. 4.

FIG. 6 is a schematic front perspective view of homogenizing tunnel 400 in FIG. 4

Figure 7:
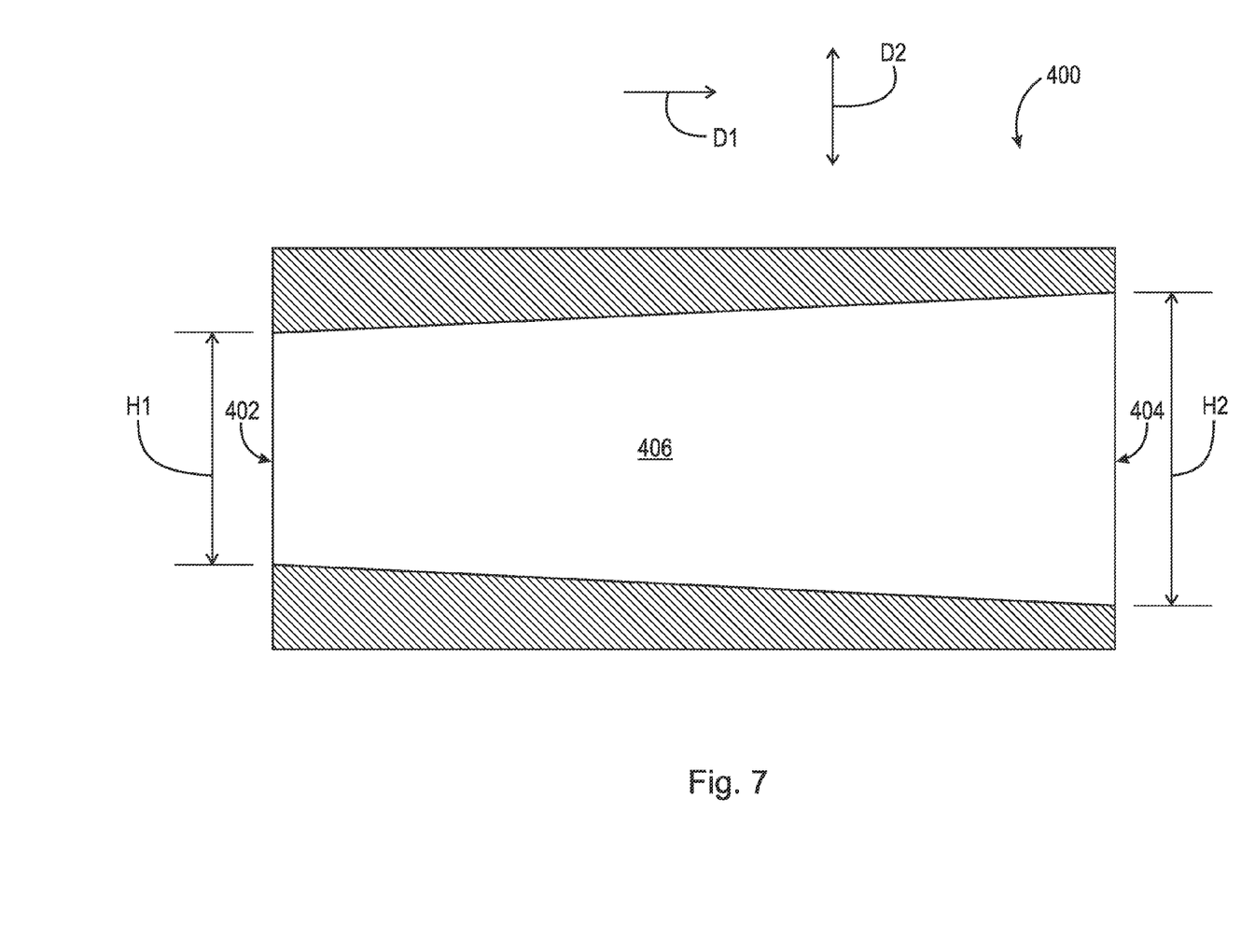
FIG. 7 is a cross-sectional view generally along line 7-7 in FIG. 5.

FIG. 7 is a cross-sectional view generally along line 7-7 in FIG. 4. Homogenizing tunnel includes apertures 402 and 404 and passageway 406 connecting apertures 402 and 404. Aperture 402 has shape 408 and size 410 and is arranged to receive extreme ultra-violet (EUV) light L from focus plane FP. Aperture 402 is congruent with plane FP. Aperture 404 has shape 412 and size 414. Passageway 406 is arranged to homogenize light L. Shape 408 is different from shape 412 or size 410 is different from size 414.

In an example embodiment, shape 408 is a square and shape 412 is a rectangle. In an example embodiment, size 414 is greater than size 410. In an example embodiment, passageway 406 tapers from aperture 404 to aperture 402. In an example embodiment (not shown), passageway 406 tapers from aperture 402 to aperture 404.

Homogenizing tunnel 400 includes longitudinal axis LA, extending in direction D1 and passing through apertures 402 and 404 and passageway 406. Aperture 402 has height H1, in direction D2, orthogonal to direction D1 and width W1, in direction D3 orthogonal to directions D1 and D2. In an example embodiment, height H1 is substantially equal to width W1; hence shape 408 is a square. Aperture 404 has height H2 in direction D2 and width W2 in direction D3. In an example embodiment, height H2 is greater than height H1 and width W2 is substantially equal to width W1; hence shape 410 is a rectangle. As a result of the difference in heights H1 and H2, passageway 406 tapers from aperture 404 to aperture 402.

In an example embodiment, system S includes plasma source PS, collector mirror M, and optics O. Source PS is arranged to generate EUV light L. Mirror M is arranged to reflect and focus light from source PS onto plane FP. Tunnel 400 is arranged to provide homogenized light HL to optics O. Optics O are arranged to convert collected photons in light HL into desired spatial and angular distribution at an illumination field (not shown). Although system S is shown with a single collector mirror M, it should be understood that a second mirror can be used to transmit and focus light L between source PS and plane FP.

As noted above, changing the properties of the plasma source in a known EUV illumination system requires the undesirable modification of the physical or optical properties of the system. Advantageously, tunnel 400 is configurable to compensate for changes in source PS without modifications to physical or optical properties. Specifically, when the properties of the plasma from source PS change, the taper of passageway 406 and the shape and size of one or both of apertures 402 and 404 can be modified to enable the physical properties of, for example system S, to remain unchanged. For example, space SP, bordered by tunnel 400, in which source PS and mirror M are located remains the same when PS is changed and/or mirror M is changed. Note that in response to changing source PS, mirror M can still be used. In this case, the magnified image of the plasma at plane FP will be different from that of the previous image. Optics O are configured according to the previous image. Therefore, the apertures and passageway of tunnel are configured to provide the required spatial and angular distribution at the aperture 404 (associated with the previous plasma source) for optics O.

Figure 8A:
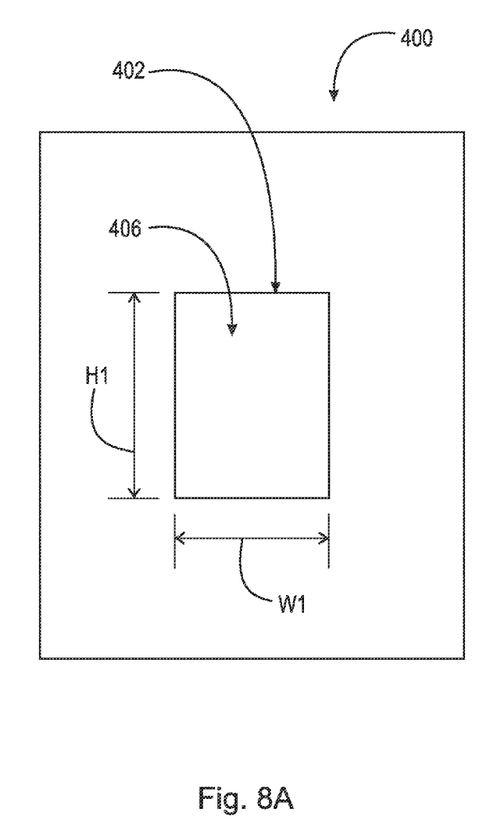
FIGS. 8A and 8B are schematic rear and front representations, respectively, of tapered homogenizing tunnel 400 with rectangular apertures.
Figure 8B:
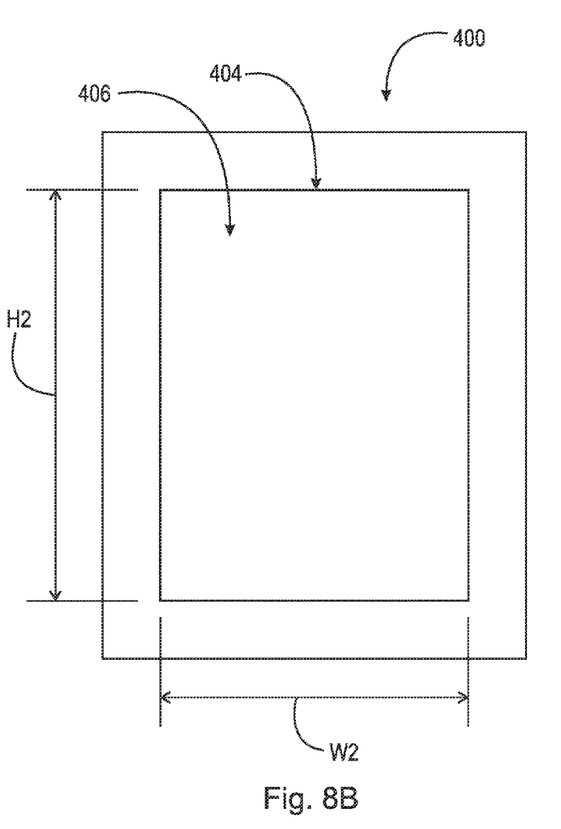

FIGS. 8A and 8B are schematic rear and front representations, respectively, of tapered homogenizing tunnel 400 with rectangular apertures. The following is an example of the use of tunnel 400. System S includes: first source PS with a diameter of 200 um; mirror M with an aperture of 0.3 NA and a magnification of 10, and a non-tapered homogenizing tunnel (not shown) with 1.5 mm×2 mm entrance aperture and 1.5 mm×2 mm exit aperture. The first source PS is replaced with a second source PS having a diameter of 100 um, and mirror M aperture extends to 0.6 NA. To compensate for these preceding changes, tunnel 400 is used with: aperture 402 having width W1 of 0.75 and height H1 of 1 mm; and aperture 404 with width W2 of 1.5 mm and height H2 of 2 mm to deliver the same spatial and angular distribution at aperture 404 as had been the case for the first source PS and without changing mirror M or space SP. Therefore, tapered tunnel 400 enables flexibility of plasma source development and photon collector design.

Returning to FIGS. 1, 2, and 3, in an example embodiment, apparatus 100 is part of semi-conductor inspection system 500 including source PS-1 and optical component 502 in focus plane 118. Optical component 502 is arranged to convert collected photons at plane 118 into desired spatial and angular distribution at an illumination field (not shown). In an example embodiment, apparatus 200 is part of semi-conductor inspection system 500 including source PS-2 and optical component 502 in focus plane 218. Optical component 502 is arranged to convert collected photons at plane 218 into desired spatial and angular distribution at an illumination field (not shown). In an example embodiment, apparatus 300 is part of semi-conductor inspection system 500 including source PS-3 and optical component 502 in focus plane 318. Optical component 502 is arranged to convert collected photons at plane 318 into desired spatial and angular distribution at an illumination field (not shown).

Figure 9:
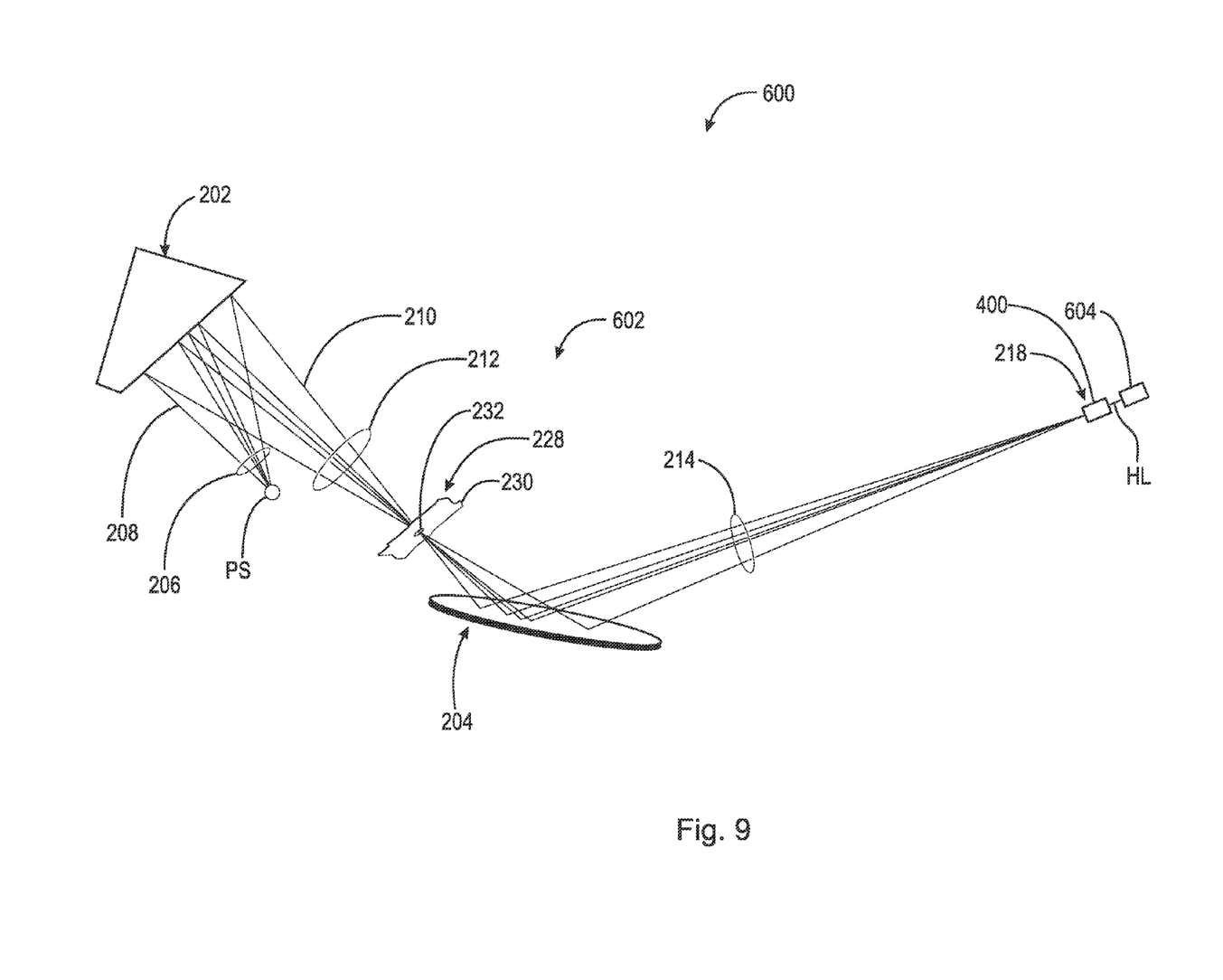
FIG. 9 is a schematic partial representation of a semi-conductor inspection system with an optical assembly and a tapering homogenizing tunnel; and, FIG. 10 is a schematic representation of a prior art illumination system for extreme ultra-violet light.

FIG. 9 is a schematic partial representation of semi-conductor inspection system 600 with optical assembly 602 and tapering homogenizing tunnel 400. System 600 includes plasma source PS arranged to generate extreme ultra-violet (EUV) light UL. In an example embodiment, assembly 602 is apparatus 200 and the discussion for FIG. 2 and apparatus 200 is applicable to FIG. 9 and assembly 602. Aperture 402 is congruent with focus plane 218. System 600 includes optical component 602 arranged to receive EUV light from plane 218 homogenized by tunnel 400. Optical component 602 is arranged to convert collected photons into desired spatial and angular distribution at an illumination field (not shown).

In FIG. 9, the configuration shown for apparatus 200 is used for assembly 602. However, it should be understood that apparatuses 100 or 300 or other two-mirror illumination and collection configurations, not illustrated herein, may be used for assembly 602. Therefore, the respective discussions for FIGS. 1, 2, and 3, regarding apparatuses 100, 200, and 300, respectively, are applicable to assembly 602. The respective discussions for FIGS. 4 through 8 regarding tunnel 400 are applicable to system 600.

The presence of plate 230 in apparatus 200 and system 600 provides at least two advantages: infrared radiation suppression and mitigation of contamination. In general, the plasma for source is generated by focusing infrared light onto the target described above. This infrared light is only partially absorbed by the target for generation of EUV radiation. The remainder of the infrared light is reflected off of the target. A portion of the reflected infrared light is reflected off of mirrors 202 and 204 and directed to optical component 602. Grating technology (not shown) is used on mirror 202 to diffract the infrared light away from aperture 232 while leaving bundle 212 relatively undisturbed. Typically, the extinction ratio for such gratings is around 50:1. Because aperture 232 is substantially the same size as the focus spot on plane 228, the vast majority of infrared light not extinguished by the grating technology is blocked by plate 230. Thus, only infrared light passing through aperture 232 is transmitted to mirror 204. The grating technology also can be applied to mirror 204 to obtain a further reduction of infrared radiation.

The environment around plasma source PS and apparatuses 100, 200, and 300 includes contaminants such as debris, fast ions, and a buffer gas, all associated with generation of the plasma and EUV light. The presence of plate 230 blocks the vast majority of the preceding contaminants, creating a much cleaner environment around mirror 204 and the downstream optical components. It is possible to size aperture 232 according to the focus spot size on the plane 228, or aperture 232 can be sized to optimize contaminant reduction.

As noted above, due to the nature of the EUV multilayer coatings used on mirrors in known EUV collection systems, the range of angle of incidence on the mirrors must be controlled. Advantageously, since the optical requirements of apparatuses 100, 200, and 300 are satisfied by two respective mirrors, rather than a single respective mirror, the respective curvatures of mirrors 102, 202, and 302 can be increased over that of typical prior art collection mirrors, resulting in an reduced range of angle of incidence. Such reduction facilitates fabrication of the coatings.

A specific level of magnification is required at each intermediate focus plane. In the prior art, the single mirror in the collection system must provide the entire magnification, increasing the range of angle of incidence, which as noted above is undesirable. The use of two respective mirrors in apparatuses 100, 200, and 300 enables the magnification to be split between the two respective mirrors, advantageously reducing the respective ranges of angle of incidence for the two mirrors.

Advantageously, apparatuses 100, 200, and 300, coupled with tapered homogenizing tunnel 400, enable the asymmetric collection of light from plasma source PS. Such collection enables optimum use of source brightness with the restrictions inherent in the coatings used on the respective mirrors.

Advantageously, tunnel 400 improves photon collection efficiency. For example, a reticle inspection tool included in system 600 requires a 3:4 rectangular illumination field and a circular pupil. However, collection of EUV light from the plasma source is more efficient with a square input aperture of the tunnel and an elliptical pupil for the EUV light. Tapered tunnel 400 enables aperture 402 to have a square shape and an elliptical pupil for more efficient collection, while tapered passageway 406 and aperture 404 are shaped to convert the input light to the 3:4 rectangular field and circular pupil.

Advantageously, tunnel 400 improves the uniformity of the illumination field. For example, for a non-tapered tunnel with a 1.5 mm×2 mm rectangular entrance, the field uniformity is better along the 1.5 mm direction than the 2 mm direction, because the narrow width induces more bounces of light rays, thus enhancing the homogenization effect. For tapered tunnel 400 with a 1 mm×1 mm aperture 402 and 1.5 mm×2 mm aperture 404, assuming an elliptical pupil at the entrance and a circular pupil at the exit, light rays bounce equally along the two directions and the homogenization effect is equal. This is a significant advantage since reticle inspection tools typically require better uniformity along the 2 mm direction than along the 1.5 mm direction.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What we claim is:

1. An apparatus for focusing light in a semi-conductor inspection system, comprising:
    a first mirror arranged to reflect extreme ultra-violet (EUV) generated by a plasma source; and,
    a second mirror arranged to focus the EUV light, reflected from the first mirror, onto a first intermediate focus plane, wherein:
        the first mirror is a positive power mirror and the second mirror is a negative power mirror; or,
        the first and second mirrors are respective positive power mirrors.

2. The apparatus of claim 1, wherein the first mirror is an elliptical concave mirror and the second mirror is a hyperbolic convex mirror.

3. The apparatus of claim 1, wherein the first mirror is arranged to focus the EUV light onto a second intermediate focus plane between the first and second mirrors.

4. The apparatus of claim 1, wherein the first and second mirrors are respective elliptical concave mirrors.

5. The apparatus of claim 1, wherein the first and second mirrors are respective parabolic mirrors.

6. The apparatus of claim 1, wherein the first mirror is arranged to focus the EUV light onto a second intermediate focus plane between the first and second mirrors.

7. The apparatus of claim 5, further comprising:
    a plate:
        including an opening with a size substantially equal to a size of the second intermediate focus plane; and,
        arranged to block transmission of debris, fast ions, or buffer gas, associated with generation of the EUV light by the plasma source, past the plate.

8. A semi-conductor inspection system, comprising:
    a plasma source arranged to generate extreme ultra-violet (EUV) light;
    a focusing assembly including:
        a first mirror arranged to reflect the EUV light from the plasma source; and,
        a second mirror arranged to focus the EUV, light reflected from the first mirror, onto a first intermediate focus plane; and,
    an optical component in the first intermediate focus plane, arranged to receive the EUV light reflected from the second mirror,
        wherein the first mirror is a positive power mirror and the second mirror is a negative power mirror; or,
        wherein the first and second mirrors are respective positive power mirrors; or,
    wherein:
        the first mirror is arranged to focus the EUV light on a second intermediate focus plane between the first and second mirrors, the system further comprising:
            a plate including an opening with a size substantially equal to a size of the second intermediate focus plane, wherein:
                the second intermediate focus plane is arranged to coincide with the opening; and,
                the plate is arranged to block transmission of debris, generated by the plasma source, past the plate.

9. The semi-conductor inspection system of claim 8, wherein:
    the EUV light travels:
        a first distance from the plasma source to the first mirror;
        a second distance from the first mirror to the second mirror; and,
        a third distance from the second mirror to the first intermediate focus plane; and,
    the second distance is greater than the third distance; or,
    the third distance is greater than the second distance.

10. A homogenizing tunnel, comprising:
    a first aperture having a first shape and a first size and arranged to receive extreme ultra-violet (EUV) light;
    a second aperture having a second shape and a second size; and,
    a passageway connecting the first and second apertures and arranged to homogenize the EUV light received by the first aperture, wherein:
        the first shape is different from the second shape; or,
        the first size is different from the second size, wherein:
    the first shape is a square and the second shape is a rectangle; or,
    the first aperture is arranged to be positioned at a focus plane to receive the EUV light focused by a mirror on the focus plane.

11. The homogenizing tunnel of claim 10, wherein:
    the homogenizing tunnel includes a longitudinal axis, extending in a first direction, passing through the first and second apertures and the passageway;
    the first aperture has:
        a first height, in a second direction orthogonal to the first direction; and,
        a first width, in a third direction orthogonal to the first and second directions, substantially equal to the first height; and,
    the second aperture has:
        a second height, in the second direction, greater than the first height; and,
        a second width, in the third direction, substantially equal to the first width.

12. The homogenizing tunnel of claim 10, wherein the second size is greater than the first size.

13. The homogenizing tunnel of claim 10, wherein:
    the passageway tapers from the first aperture to the second aperture; or,
    the passageway tapers from the second aperture to the first aperture.

14. A semi-conductor inspection system, comprising:
    a plasma source arranged to generate extreme ultra-violet (EUV) light;
    an illuminating apparatus including at least one mirror arranged to reflect the EUV light from the plasma source and focus the EUV light onto a first intermediate focus plane; and, a homogenizing tunnel including:
  a first aperture positioned at the first intermediate focus plane and having a first shape and a first size;
  a second aperture having a second shape and a second size; and,
  a passageway connecting the first and second apertures, wherein:
  the EUV light focused by the second mirror at the first intermediate focus plane is arrange to enter the homogenizing tunnel at the first aperture and exit the homogenizing tunnel at the second aperture; and,
  the first shape is different from the second shape; or,
  the first size is different from the second size.

15. The semi-conductor inspection system of claim 14, wherein the at least one mirror includes:
  a first mirror arranged to reflect the EUV light from the plasma source; and,
  a second mirror arranged to focus the EUV light, reflected from the first mirror, onto the first intermediate focus plane.

16. The semi-conductor inspection system of claim 15, wherein:
  the first mirror is a positive power mirror and the second mirror is a negative power mirror; or,
  the first and second mirrors are respective positive power mirrors.

17. The semi-conductor inspection system of claim 14, wherein:
  the first shape is a square; and,
  the second shape is a rectangle.

18. The semi-conductor inspection system of claim 14, wherein the second size is greater than the first size.

19. The semi-conductor inspection system of claim 14, wherein:
  the passageway tapers from the first aperture to the second aperture; or,
  the passageway tapers from the second aperture to the first aperture.

20. A method for focusing light in a semi-conductor inspection system, comprising:
  reflecting, using a first mirror, extreme ultra-violet (EUV) light generated by a plasma source;
  focusing, using a second mirror, the EUV light reflected from the first mirror, onto a first intermediate focus plane for use in a semi-conductor inspection system;
  placing a second intermediate focus plane substantially in an opening in a barrier; and,
  transmitting the light focused by the second mirror through the opening.

21. The method of claim 20, further comprising:
  focusing, using the first mirror, the EUV light onto the second intermediate focus plane between the first and second mirrors.

22. The method of claim 20, further comprising:
  blocking, with the barrier, debris, fast ions, or buffer gas associated with generation of the EUV light by the plasma source, past the plate.

23. A method for homogenizing light in a semi-conductor inspection system, comprising:
  focusing, onto a first intermediate focus plane and using at least one mirror, extreme ultra-violet (EUV) light generated by a plasma source;
  transmitting the EUV light focused on the first intermediate focus plane into a first aperture of a homogenizing tunnel;
  transmitting the EUV light focused on the first intermediate focus plane along a tapered passageway for the homogenizing tunnel;
  reflecting the EUV light focused on the first intermediate focus plane from a plurality of surfaces of the passageway; and,
  transmitting the EUV light focused on the first intermediate focus plane and the EUV light reflected from the plurality of surfaces out of the homogenizing tunnel through a second aperture of the tunnel for use in a semi-conductor inspection system.

24. The method of claim 23, wherein:
  transmitting the EUV light focused onto the first intermediate focus plane into a first aperture of a homogenizing tunnel includes transmitting the EUV light focused onto the first intermediate focus plane into the first aperture having a first shape or a first size; and,
  transmitting the EUV light focused onto the first intermediate focus plane and the EUV light reflected from the plurality of surfaces out of the homogenizing tunnel through a second aperture of the tunnel includes transmitting the EUV light focused onto the first intermediate focus plane and the EUV light reflected from the plurality of surfaces out of the homogenizing tunnel through the second aperture of the tunnel having:
    a second shape different from the first shape; or,
    a second size different from the first size.

25. The method of claim 23, wherein:
  transmitting the EUV light focused onto the first intermediate focus plane into a first aperture of a homogenizing tunnel includes transmitting the EUV light focused onto the first intermediate focus plane into the first aperture having a square shape; and,
  transmitting the EUV light focused onto the first intermediate focus plane and the EUV light reflected from the plurality of surfaces out of the homogenizing tunnel through a second aperture of the tunnel includes transmitting the EUV light focused onto the first intermediate focus plane and the EUV light reflected from the plurality of surfaces out of the homogenizing tunnel through the second aperture of the tunnel having a rectangular shape.

26. The method of claim 23, wherein transmitting the EUV light focused onto the first intermediate focus plane along a tapered passageway for the homogenizing tunnel includes transmitting the EUV light focused onto the first intermediate focus plane along the tapered passageway tapering from the second aperture to the first aperture.

27. The method of claim 23, wherein focusing, onto the first intermediate focus plane and using the at least one mirror, EUV light generated by the plasma source includes
  includes reflecting the EUV light with one single mirror or with first and second mirrors.

28. A method for focusing light in a semi-conductor inspection system, comprising:
  generating first extreme ultra-violet (EUV) light using a first plasma source having a first intensity and a first angular distribution of intensity;
  focusing, using first and second mirrors, the first EUV light onto an intermediate focus plane for use in semi-conductor inspection;
  generating second extreme ultra-violet (EUV) light using a second plasma source having a second intensity or a second angular distribution of intensity;
  focusing, using third and fourth mirrors, different from the first and second mirrors respectively, the second EUV light onto the intermediate focus plane, wherein:

the first plasma source and the first and second mirrors occupy a first minimum space within the semi-conductor inspection system;

the second plasma source and the third and fourth mirrors occupy a second minimum space within the semi-conductor inspection system; and, the first minimum space is substantially equal to the second minimum space.

29. The method of claim 28, wherein:

a position of the intermediate focus plane is fixed with respect to a plane defined by first and second directions orthogonal to each other;

one of the first plasma source or the first mirror is furthest from the intermediate focus plane in the first direction;

the second mirror is between the first mirror and the intermediate focus plane in the first direction;

one of the second plasma source or the third mirror is furthest from the intermediate focus plane in the first direction;

the fourth mirror is between the third mirror and the intermediate focus plane in the first direction;

the one of the first plasma source or the first mirror is a first distance from the intermediate focus plane in the first direction; and, the one of the second plasma source or the third mirror is a second distance, substantially equal to the first distance, from the intermediate focus plane in the first direction.

30. A method for focusing light in a semi-conductor inspection system, comprising:

generating first extreme ultra-violet (EUV) light using a first plasma source having a first intensity and a first angular distribution of intensity;

focusing, using at least one first mirror, a first image, with a first size, of the first EUV light onto an intermediate focus plane;

transmitting the first EUV light, as a first image, through a first tapering passageway for a first homogenizing tunnel with a first entrance aperture congruent with the intermediate focus plane;

transmitting, from an exit aperture for the first tunnel, the first EUV light as the first image with the first size for use in the semi-conductor inspection system;

generating second extreme ultra-violet (EUV) light using a second plasma source having a second intensity or a second angular distribution of intensity;

focusing, using the at least one second mirror, a second image, with a second size different from the first size, of the second EUV light onto the intermediate focus plane;

transmitting the second EUV light, as the second image, through a second tapering passageway for a second homogenizing tunnel with a second entrance aperture congruent with the intermediate focus plane; and, transmitting, from an exit aperture for the first tunnel, the second EUV light as the second image with the first size for use in the semi-conductor inspection system, wherein:

a position of the intermediate focus plane is fixed with respect to the semi-conductor inspection system; and, the at least one first mirror and the at least one second mirror are in the same respective positions; or, a first minimum space occupied by the at least one first mirror is substantially equal to a second minimum space occupied by the at least one second mirror.

* * * * *